(12) United States Patent
Maurice et al.

(10) Patent No.: US 11,719,812 B2
(45) Date of Patent: Aug. 8, 2023

(54) ULTRASOUND SYSTEM

(71) Applicant: SUPERSONIC IMAGINE, Aix en Provence (FR)

(72) Inventors: François Maurice, Draguignan (FR); Claude Cohen Bacrie, Aix en Provence (FR); Mathieu Couade, Aix en Provence (FR)

(73) Assignee: SuperSonic Imagine, Aix-en-Provence (FR)

( * ) Notice: Subject to any disclaimer, the term of this patent is extended or adjusted under 35 U.S.C. 154(b) by 171 days.

(21) Appl. No.: 17/427,798

(22) PCT Filed: Feb. 7, 2020

(86) PCT No.: PCT/EP2020/053105
§ 371 (c)(1),
(2) Date: Aug. 2, 2021

(87) PCT Pub. No.: WO2020/161287
PCT Pub. Date: Aug. 13, 2020

(65) Prior Publication Data
US 2022/0128687 A1  Apr. 28, 2022

(30) Foreign Application Priority Data

Feb. 7, 2019  (EP) ..................... 19305145

(51) Int. Cl.
| | | |
|---|---|---|
| *G01S 15/89* | (2006.01) | |
| *A61B 8/00* | (2006.01) | |
| *G10K 11/30* | (2006.01) | |
| *G10K 11/34* | (2006.01) | |

(52) U.S. Cl.
CPC .......... *G01S 15/8952* (2013.01); *A61B 8/469* (2013.01); *G01S 15/8954* (2013.01); *G10K 11/30* (2013.01); *G10K 11/343* (2013.01)

(58) Field of Classification Search
CPC . G01S 15/8952; G01S 15/8954; A61B 8/469; G01K 11/30; G01K 11/343
See application file for complete search history.

(56) References Cited

U.S. PATENT DOCUMENTS

| | | |
|---|---|---|
| 4,351,038 A | 9/1982 | Alais |
| 5,795,311 A | 8/1998 | Wess |
| (Continued) | | |

FOREIGN PATENT DOCUMENTS

| | | |
|---|---|---|
| GB | 2 114 296 A | 8/1983 |
| WO | 2013/017105 A1 | 2/2013 |

OTHER PUBLICATIONS

International Search Report and Written Opinion of the International Searching Authority for International Patent Application No. PCT/EP2020/053105 dated Apr. 21, 2020, 10 pages.

(Continued)

*Primary Examiner* — Dixomara Vargas
(74) *Attorney, Agent, or Firm* — Merchant & Gould P.C.

(57) ABSTRACT

An ultrasound system comprising a probe adapted for emitting and receiving ultrasound waves inside a medium, and a processing unit connected to said probe and adapted for processing signals from the probe. The probe is configured so as to behave as a Fresnel lens for focusing the ultrasound waves. The processing unit analyses signals from the probe for sensing the medium at a plurality of focal points.

16 Claims, 4 Drawing Sheets

(56) References Cited

U.S. PATENT DOCUMENTS

2009/0118619 A1  5/2009  Oshiki
2013/0218012 A1  8/2013  Specht et al.

OTHER PUBLICATIONS

Partial European Search Report for European Patent Application No. 19305145.5 dated Jul. 31, 2019, 12 pages.
Extended European Search Report for European Patent Application No. 19305145.5 dated Oct. 21, 2019, 13 pages.
Jian, X. et al., "Design of micromachined self-focusing piezoelectric composite ultrasound transducer", 2014 36th Annual International Conference of the IEEE Engineering in Medicine and Biology Society, 550-553 (Aug. 2014).

ULTRASOUND SYSTEM

This application is a National Stage Application of PCT/EP2020/053105, filed 7 Feb. 2020, which claims benefit of European Patent Application Serial No. 19305145.5, filed 7 Feb. 2019, and which applications are incorporated herein by reference. To the extent appropriate, a claim of priority is made to each of the above disclosed applications.

FIELD OF THE INVENTION

The present invention concerns an ultrasound system for sensing a medium.

BACKGROUND OF THE INVENTION

The present invention concerns more precisely an ultrasound system comprising:
- a probe adapted for being put into contact with a medium and comprising at least one transducer adapted for emitting and receiving ultrasound waves in said medium, and
- a processing unit associated to said probe and adapted for processing signals from the probe.

It is known to use such ultrasound imaging system to generate an image.

However, such system needs to have a probe with numerous transducers, for example more than 100 transducers, and to process a complex beamforming during emitting and/or receiving of ultrasound waves. The beamforming process at least consists of applying an amplification factor and a delay independently to each signal from/to each transducer so as to focalize ultrasound energy to various points inside the medium. Such system therefore comprises as many analog to digital converter (ADC) channels as the number of transducers in the probe. Such system is then complex and expensive.

There is consequently a need for a cheap and easy to use system.

OBJECTS AND SUMMARY OF THE INVENTION

One object of the present invention is to provide an ultrasound system that is much less expensive than prior art to sense a region of interest inside a medium.

To this end, the ultrasound system further has the following features:
- the probe (12) is not axisymmetric and is a linear probe extending according to a longitudinal direction,
- the probe comprises at least one portion comprising along the longitudinal direction a plurality of probe sections having a width that decrease from a first end to a second end of said portion so as to behave as a Fresnel lens in that the probe focusses the ultrasound waves towards and from a focal point inside the medium, said focal point being different for each frequency of said ultrasound waves,
- the processing unit analyses signals received from said probe at a plurality of frequencies around a nominal frequency for sensing the medium at a plurality of focal points situated in the medium, and
- the processing unit (13) builds an image of the medium on the bases of a plurality of focal points sensed in the medium, the image being composed of a grid of pixels, the pixels aligned in the longitudinal direction (X) being determined by the signals at the plurality of frequencies, and the pixels aligned in the depth direction (Z) perpendicular to the longitudinal direction being determined by the level of the signals received for a plurality of time of flight between the probe and focal point in the medium.

Thanks to the use of a probe having a Fresnel lens effect for focussing inside the medium and thanks to the processing unit that analyses a plurality of frequencies of received ultrasound waves, the ultrasound system is able to sense a region of interest of the medium. The quality of a produced image might be decreased compared to prior art systems having a huge number of transducers, but the produced quality might be enough for the user. The system is advantageously much simpler and is less expensive than these prior art systems.

In various embodiments of the disclosed ultrasound system, one and/or other of the following features may optionally be incorporated.

According to an aspect, the processing unit controls the probe to emit successively at the plurality of frequencies to move the focal point in the medium, and the processing unit analyses the signals received for each of said frequencies for sensing the medium at said focal points.

According to an aspect, the processing unit controls the probe to emit a ultrasound wave having a broadband characteristic around the nominal frequency, and filters the signals at a plurality of frequencies for sensing the medium at said plurality of focal points.

According to an aspect, the processing unit builds an image of the medium on the bases of a plurality of focal points sensed in the medium.

According to an aspect:
the probe comprises one transducer and a lens layer disposed above said transducer, the lens layer being composed of a plurality of sections forming a quasi-saw tooth shape, each section having a step length in the direction of the nominal focal point that is equal to a distance defined so that an ultrasound wave emitted by the transducer in the medium through the lens layer has a phase difference of $2 \cdot k \cdot \pi$ between a portion of wave emitted though one section and a portion of wave emitted by a neighbour section, next to said one section, k being an integer greater or equal to one.

According to an aspect, the step length is equal to:

$$SL = \lambda_{lens} \cdot c_{medium} / (c_{medium} - c_{lens})$$

where
$c_{medium}$ is a speed of ultrasound wave inside the medium,
$\lambda_{lens} = c_{lens}/f_n$ is the lens wavelength $\lambda_{lens}$,
$c_{lens}$ is a speed of ultrasound wave inside the material of the lens layer, and
$f_n$ is the nominal frequency of the ultrasound wave adapted for focusing to the nominal focal point $FP_n$.

According to an aspect:
the probe comprises a plurality of transducers that are configured so as any pair of two transducers that are neighbour one to the other have a focal point difference distance equal to the wavelength divided by a period number p, said period number p being an integer greater or equal to two, the focal point difference distance being an absolute value of a difference between a first distance between the nominal focal point and the first transducer belonging to the pair and a second distance between the nominal focal point and the second transducer belonging to the pair, and
the system adds signals from transducers that are p-spaced one to another to form p phased signals.

According to an aspect, the focal point difference distance is determined as follow:

$$D_{fpd}=|d(FP,T_i)-d(FP,T_{i+1})|=\lambda/p$$

where
d(FP,T$_i$) is the first distance,
d(FP,T$_{i+1}$) is the second distance,
i is an index of any transducer,
k is the wavelength, and
p is the period number.

According to an aspect, the p-spaced transducers are connected together with short circuits to add the signals from said p-spaced transducers to form the phased signals.

According to an aspect, the period number is equal to four.

According to an aspect, the probe further comprises a patterned lens layer positioned above the transducers and arranged to be put in contact with the transducers and with the medium.

According to an aspect, the patterned lens layer is a prismatic shape, having a thickness that increases on the side of the transducer that corresponds to the shortest distance to the nominal focal point.

According to an aspect, the probe comprises two portions, a first portion situated on a first side in comparison to a depth direction, said depth direction being perpendicular to the longitudinal direction, and a second portion situated on a second side of said depth direction.

According to an aspect, the first portion and second portion are symmetric relative to the depth direction, the first portion and second portion each have a nominal focal point, and said nominal focal points are identical.

According to an aspect, the processing unit builds a first image with signals from the first portion and a second image with signals from the second portion, said first and second images not overlapping each other, the first image corresponding to a first quadrant in the medium defined in the first side relative to the depth direction, and the second image corresponding to a second quadrant in the medium defined in the second side relative to the depth direction.

According to an aspect, the probe further comprises at least one additional transducer situated between the first and second portions.

According to an aspect, the additional transducer is adapted for generating a vibration propagating inside the medium at a low frequency, said vibration being sensed by the first portion and second portion of the probe, and the processing unit calculates at least one value of elasticity inside the medium on the bases of displacement of said vibration in the medium.

BRIEF DESCRIPTION OF THE DRAWINGS

Other features and advantages of the invention will be apparent from the following detailed description of several of its embodiments given by way of non-limiting examples, with references to the accompanying drawings that are provided for illustration purposes. In the drawings.

MORE DETAILED DESCRIPTION

Figure 1:
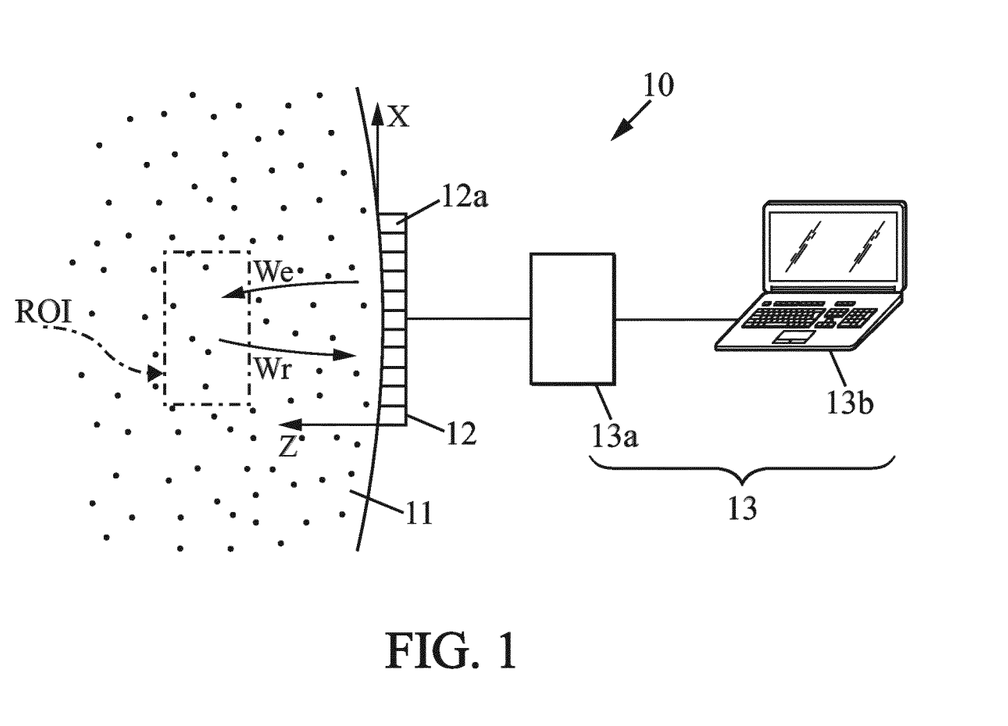
FIG. 1 is a schematic general view of an ultrasound system.

FIG. 1 shows an ultrasound system 10 according to the disclosure and adapted for sensing a region of interest ROI inside a medium 11. The ultrasound system may build an image of at least a portion of the region of interest, as it will be explained in the following description.

The medium 11 is for instance a living body and in particular human or animal bodies, or it can be any other biological or physic-chemical medium (e.g. in vitro medium). The volume of medium comprises variations in its physical properties. For example, the medium may comprise tissues and blood vessels, each one having various physical properties. For example, the tissue may comprise an area suffering from an illness (e.g. cancerous cells), or any other singular area, having various physical properties in comparison to other area of the medium. Some portions of the medium 11 may include some added contrast agent (e.g. micro bubbles) for improving the contrast of physical properties of these portions.

The ultrasound system 10 may include:
- a probe 12 put into contact with the medium 11 to be imaged (for at least a duration of some seconds), and comprises one ultrasound transducer or a plurality of ultrasound transducers (i.e. a transducer array), each transducer 12a being adapted to transform a signal into an ultrasound wave (emit mode) and/or to transform an ultrasound wave into a signal (receive mode),
- a processing unit 13 associated to the probe 12 for controlling the transducers 12a in the probe 12, and for processing the signal(s) by various processes, in order to sense the medium and optionally to generate an least one or several images of a portion of the region of interest of the medium.

More precisely, the processing unit 13 can control the probe 12 by providing signal(s) to the probe for emitting the emitting ultrasound waves, and by receiving signal(s) from the probe 12 corresponding to ultrasound waves arriving on the probe 12 from the medium.

The processing unit 13 then may sense and/or generate an image of the region of interest ROI inside the medium 11 on the bases of said signal(s).

In an embodiment, the processing unit 13 may be divided into two devices, an electronic unit 13a for controlling the transducer(s) and converting the signal(s) into data, and a computer 13b for processing the converted data.

The probe 12 may be a linear array of transducers. The focussing towards a predetermined position in the medium in front of the probe is performed by phasing the signals. The probe may comprise a number N of transducers 12a, e.g. few tens of transducers (for instance 100 to 300) juxtaposed along a longitudinal direction or axis X so as to perform ultrasound focussing into a bi-dimensional (2D) plane. The probe 12 can comprise a bi-dimensional array so as to perform ultrasound focussing into a tri-dimensional (3D) volume.

The processing unit 13 usually comprise a processor, a memory containing instruction codes for implementing of the method for processing the data, a keyboard and a display for displaying the generated images.

Each transducer 12a emits and/or receives ultrasound waves that can have a broadband characteristic inside a wide frequency bandpass Δf around a predetermined central frequency f.

The ultrasound waves have a central wavelength λ that is equal to λ=c/f where f is the predetermined central frequency, and c is the speed of ultrasound waves inside the medium 11.

The emitted ultrasound waves We, emitted by the probe 12, propagate from the probe, inside the medium 11, in a direction substantially perpendicular to the longitudinal direction X, i.e. in a depth direction Z, and toward the region of interest ROI. Scatters in the medium 11 reflect these waves that are returned toward the probe 12 as received ultrasound waves Wr.

In the following description of the disclosed embodiments:
the probe 12 is non axisymmetric and it is a probe linear, extending according to the longitudinal direction X,
the probe 12 comprises at least one portion comprising along the longitudinal direction X a plurality of probe sections having a width that decrease from a first end to a second end of said portion, so as to behave as a Fresnel lens in that the probe focusses the ultrasound waves towards and from a focal point FP inside the medium, said focal point being different for each frequency of said ultrasound waves,
the processing unit 13 analyses the signals received from said probe at a plurality of frequencies $f_j$ around a nominal frequency $f_n$ for sensing the medium at a plurality of focal points $FP_j$ situated in the medium, and
the processing unit 13 builds an image of the medium on the bases of a plurality of focal points sensed in the medium, the image being composed of a grid of pixels, the pixels aligned in the longitudinal direction X being determined by the signals at the plurality of frequencies, and the pixels aligned in the depth direction Z being determined by the level of the signals received for a plurality of time of flight between the probe and the focal point in the medium.

The probe 12 according to the disclosure is not an "axisymmetric probe" in the meaning that an axisymmetric probe has an axisymmetric axis and concentric elements organized around said axis, such as a concentric shaped lens or concentric shaped ultrasound transducers. These so called "axisymmetric" probes are usually used to focus high level of energy at an accurate location (one focal point) for medical treatment of this location inside the medium. Some probes of this kind can vary the depth of the focal point by varying the ultrasound frequency. But, these axisymmetric probes are not used in an ultrasound system to produce a two dimensional image of a medium, because of the symmetry of such probe that focusses the ultrasound waves on the axisymmetric axis. This necessitates adding a mechanical displacement device to move the probe itself at least along one or two directions (X, Y). This solution is as a consequence too complex in use.

By "probe", it is understood the active part that emit and/or receive the ultrasound wave. We do not consider the casing that maintains the active part and that is adapted to the hand of user for holding it.

By "linear probe", it is understood a probe that extends in the longitudinal direction X, i.e. having the active part that mainly extends in the longitudinal direction. The aim of such probe is to deliver signal for imaging an ROI of the medium 11 according to an X-Z plane. In a transversal direction Y perpendicular to the longitudinal direction X and to the depth direction Z, the probe size is much smaller than in the longitudinal direction X. This probe size can be a small constant, such as a millimeter or few millimeters (eg. Less than 10 mm), or can be dependent on the abscissa in the longitudinal direction X.

Therefore, the probe 12 of the current disclosure is not an axisymmetric probe and this probe 12 is a linear probe. The probe 12 comprises probe sections in a lens layer or in the transducer(s) layer having widths that are not all equal (not regularly spaced), and that increase from a first end to a second end of the probe 12. Thanks to these probe sections, the probe 12 is not periodic in the longitudinal direction X. The probe 12 is also not symmetric relative to a direction perpendicular to the longitudinal direction X. The features of the probe sections will be more explained in the following disclosed embodiments.

The probe 12 then behaves as a Fresnel lens: it is a Fresnel linear device. Such probe 12 is then adapted so that the ultrasound system using such probe can provide a two dimensional image (in X-Z plane) of the medium 11.

Figure 2:
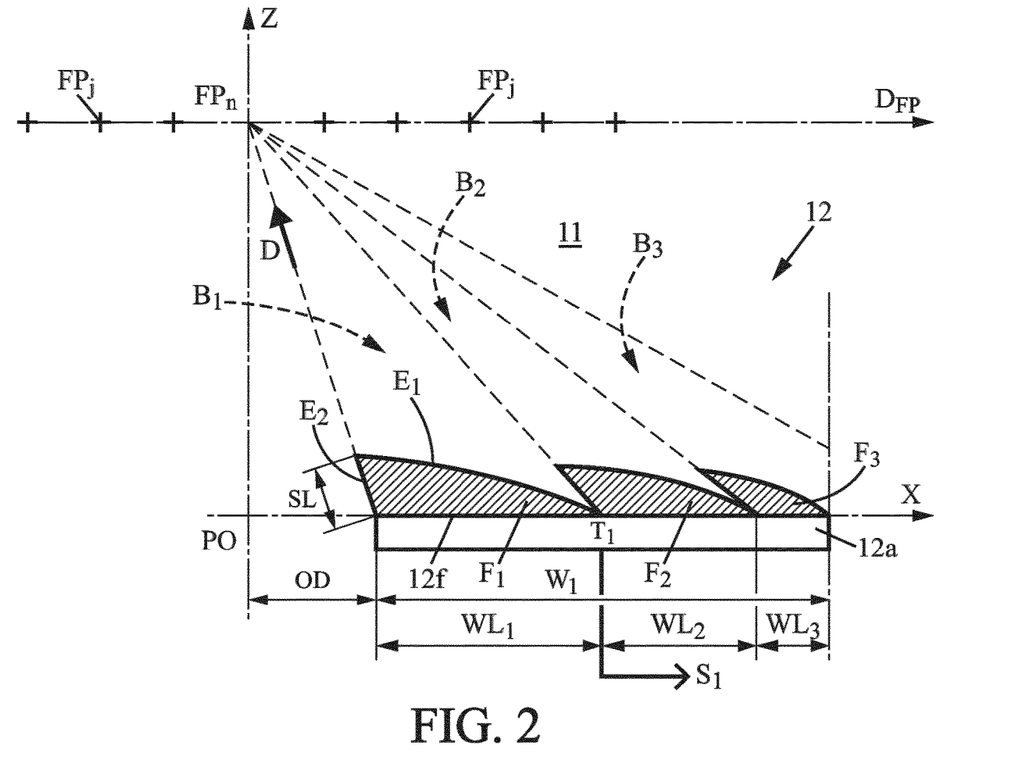
FIG. 2 is a schematic view of a first embodiment of a system according to the invention.
Figure 2A:
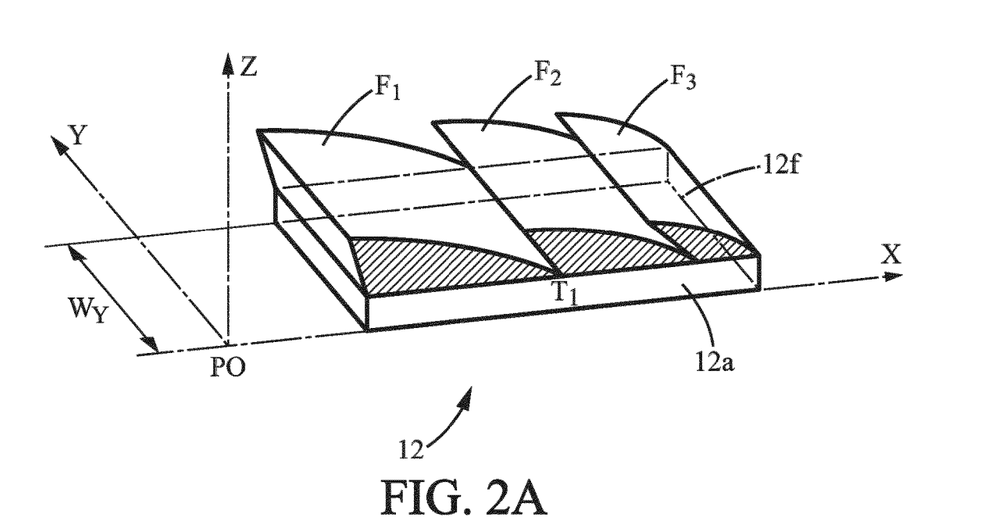
FIG. 2A is a perspective view of the probe of FIG. 2.

FIG. 2 shows a view in the X-Z plane of the probe according to an embodiment of the disclosure. FIG. 2A shows the probe of FIG. 2 in a perspective view illustrating that the probe of the current disclosure is not an axisymmetric probe and that this probe is a linear probe aligned in the longitudinal direction X.

In this embodiment, the probe 12 comprises:
one transducer 12a, also referred as $T_1$ on the FIG. 2, and
a lens layer 12f disposed above said transducer so as to be in contact with the transducer 12a and with the medium 11.

The lens layer 12f is in this example a focussing layer secured above the transducer 12a.

The transducer 12a for example transforms mechanical strain in the depth direction Z (said strain corresponding to waves in the medium) into an electric signal $S_1$, and reciprocally.

The lens layer 12f has a general shape that may be approximatively a curved saw tooth. Then, the lens layer 12f is composed of a plurality of sections $F_1, F_2, F_3 \ldots,$ and $F_k$. Each section is a convex curved shape with:
a first edge E1 that is a surface facing a nominal focal point $FP_n$ situated inside the region of interest ROI in the medium 11 (the first edge E1 surface is a convex surface oriented to the nominal focal point $FP_n$, i.e. oriented in a direction D towards said nominal focal point $FP_n$), and
a second edged E2 that is a surface substantially parallel to the direction D towards the nominal focal point $FP_n$ (i.e. a direction normal to said surface of second edge E2 is perpendicular to the direction D).

On FIGS. 2 and 2A, the sections $F_1, F_2, F_3 \ldots,$ and $F_k$ of the lens layer 12f correspond to the probe sections having a width that decrease from a first end (left side of probe 12 on FIG. 2) to a second end (right side of probe 12 on FIG. 2) of the probe: the widths $wL_1, wL_2, wL_3, \ldots$.

Each first edge E1 of the sections $F_1, F_2, F_3 \ldots,$ and $F_k$ emits to and/or receives from the nominal focal point $FP_n$, an ultrasound wave respectively forming a beam $B_1, B_2, B_3 \ldots,$ and $B_k$ inside the medium. Each second edge E2 does not substantially contribute to the ultrasound waves, because its surface is not oriented to the nominal focal point $FP_n$.

The surface of the second edge E2 might not be exactly oriented perpendicularly to the direction D for various reasons, such as manufacturing reasons. However, its projected surface in the direction D is much smaller than the projected surface of the first edge E1, for example less than 10% thereof. The second edge does not contribute to the ultrasound waves propagating towards and from the nominal focal point $FP_n$ whereas the first edge E1 is the surface that mainly or quasi-totally contribute to the ultrasound waves propagating towards and from the nominal focal point $FP_n$.

The beams $B_1, B_2, B_3 \ldots$, and $B_k$ are inclined relative to the longitudinal direction X and substantially according to the above direction D. The depth direction Z is perpendicular to the longitudinal direction X and it goes through the nominal focal point $FP_n$. A point of origin PO is defined as the intersection of the depth direction Z and the longitudinal direction X. The point of origin PO is then for example distant from a lateral edge of the transducer 12a, in the longitudinal direction X of an offset distance OD. This means that the beams are inclined and that the nominal focal point $FP_n$ is not exactly above the probe 12. The transducer 12a is laterally shifted in the longitudinal direction X of said offset distance OD in comparison to the original point OP.

The first edge E1 may be planar or curved, e.g. a convex shape relative to the nominal focal point $FP_n$ inside the medium 11.

The second edge E2 is potentially planar, and it is a step in the direction D, i.e. in the direction of the nominal focal point $FP_n$, said step having a step length SL.

The step length SL is approximately equal to a distance so that an ultrasound wave emitted by the transducer in the medium through the lens layer 12f has a phase difference of $2 \cdot \pi$ between a portion of wave emitted though one section $F_k$ and a portion of wave emitted by a neighbour section $F_{k+1}$, next to said one section $F_k$, k being an integer as $1<=k<=N$, N being the number of sections of the lens layer 12f.

According to a model, the step length SL is for example equal to:

$$SL = \lambda_{lens} \cdot c_{medium} / (c_{medium} - c_{lens}) \quad (Eq. 1)$$

where $c_{medium}$ is a speed of ultrasound wave inside the medium 11, $\lambda_{lens} = c_{lens}/f_n$ is the lens wavelength $\lambda_{lens}$, (i.e. wavelength of waves in the lens), $c_{lens}$ is a speed of ultrasound wave inside the material of the lens layer, and $f_n$ is a nominal frequency of the ultrasound wave adapted for focusing to the nominal focal point $FP_n$.

Thanks to the above geometry of the lens layer 12f, the lens layer 12f behaves as a Fresnel lens that focusses the ultrasound waves towards and from the nominal focal point $FP_n$ inside the medium 11.

As illustrated on FIG. 2A, the probe 12 is a linear probe extending along longitudinal direction X, said probe having one transducer 12a and a lens layer 12f having sections $F_1$, $F_2$, $F_3 \ldots$, and $F_k$ and forming the probe sections. Such probe 12 is not axisymmetric, and is not symmetric. Therefore, contrary to axisymmetric probes, such probe 12 is able to focus to various focal points $FP_j$ that can be shifted laterally in the longitudinal direction X (direction of such linear probe).

The probe 12 has for example a width in the transversal direction Y, a constant width $w_Y$, as disclosed on FIG. 2A. However, in another embodiment, such transversal width $w_Y$ can vary along the abscissa in the longitudinal direction X. For example, the transversal width can increase from the first end (left side of probe 12 on FIG. 2) to the second end (right side of probe 12 on FIG. 2) of the probe 12.

This embodiment may then use a lens layer 12f above a single transducer 12a. The transducer 12a is subjected to all the ultrasound waves arriving from all sections of lens layer 12f, and the transducer 12a combines these ultrasound waves to provide a single electric signal $S_1$ that is transmitted to the processing unit 13.

The processing unit 13 is defined as being able to activate the transducer 12a according to various signals for emitting the emitting ultrasound waves. The emitted ultrasound waves may be:

a sinus wave generated at a frequency f that can be changed (i.e. shifted) to a plurality of frequencies $f_j$ around the nominal frequency $f_n$; or a broadband wave comprised inside the frequency bandpass $\Delta f$; or a wave composed of a sum of a plurality of sinus waves, or a timely variant sinus wave, or a plurality of them.

Then, the processing unit 13 analyses signals received from the probe 12 at a plurality of frequencies $f_j$ around the nominal frequency $f_n$ for sensing the medium at a plurality of focal points $FP_j$ situated in the medium, j being an index of said specific frequency corresponding to a specific focal point, j being an integer.

Optionally, the processing unit 13 generates a plurality of identical emitting sequences of ultrasound waves (e.g. at the same frequency), receives a plurality of signals corresponding to receiving sequences that result from said emitting sequences, and calculate an averaging of said plurality of signals. The processing unit 13 then analyses said averaged signal as it is a received signal for sensing the medium This improves the signal to noise ratio.

In a first variant and for the sake of simplicity, the process will be explained in the case of a sinus wave at frequency f.

The processing unit 13 is able to change the frequency f of the emitted ultrasound waves to a plurality of frequencies $f_j$. Thanks to this frequency change (i.e. frequency shift), the inclination of beams is modified, and the focal point is moved inside the medium 11 towards other focal points $FP_j$ corresponding to said frequencies $f_j$, these other focal points being aligned on a direction of focal points $D_{FP}$. For the sake of simplicity, the successive other focal points represented on the figures (the locus of the successive other focal points) are aligned according to a straight line, but they may be aligned in some embodiments according to a curved line when frequency is changed. Ideally, the direction (locus) of focal points $D_{FP}$ is substantially parallel to the longitudinal direction X. Alternatively; the direction (locus) of focal points $D_{FP}$ may be inclined relative to the longitudinal direction, depending on geometry of lens layer 12f. For example, when the frequency is increased, the other focal points $FP_j$ are moving laterally in the direction $D_{FP}$, i.e. substantially in a direction parallel to the longitudinal direction X, or according to a curved line predetermined by at least the characteristics of the lens layer 12f. In a similar way, when the frequency is decreased, the other focal points $FP_j$ are moving laterally in the direction $D_{FP}$, on the opposite side of the depth direction Z However, the beams associated to the other focal points $FP_j$ might not be as well focussed as for the nominal focal point $FP_n$. Moreover, the excitation of transducer(s) is a narrow bandwidth and a quasi-pure frequency. These imperfections and limitations may lead to pixels in the calculated image that are blurrier compared to pixels from a usual ultrasound imaging technique and/or compared to a pixel corresponding to a point in the medium at the nominal focal point $FP_n$.

Then, the processing unit 13 analyses the signals received for each one of the plurality of frequencies $f_j$ for sensing the medium at corresponding plurality of focal points $FP_j$ along said direction (locus) of focal points $D_{FP}$.

Then, the processing unit 13 may also be able to calculate an image of a region of interest inside the medium on the bases of signals received from the probe at the plurality of frequencies $f_j$. The image is for example composed of a grid of pixels in X-Z directions. It is understood that the pixels aligned in the X direction are approximately determined by varying the frequency f and the pixels aligned in the Z direction are approximately determined by the level of signal received for each time of flight (distance to transducer).

By "a grid of pixels", it may be understood a matrix of pixel values (image) that can correspond to a matrix of locations in the medium 11. The matrix of locations can be spatially equally spaced or not. Optionally, the matrix of locations can be associated the matrix of pixel values to define any shape of image (not only a square or a rectangle). Optionally, the location of the pixel can be anywhere inside the medium 11.

In a second variant, the processing unit 13 is able to control the probe 12 to emit in the medium 11 an ultrasound wave having a broadband signal characteristic around the nominal frequency $f_n$.

In that case, the probe 12 behaves as if it simultaneously focusses to a plurality of focal points $FP_j$ inside the medium corresponding to the bandwidth of said signal.

Then, the processing unit 13 filters the received signal from the transducer 12a in response to the emitted broadband signal (corresponding to the emitted wave) so as to sense the medium at said plurality of focal points. Then, the processing unit 13 may determine at least an image of the medium on the bases of said plurality of focal points sensed by the system. The filter is advantageously a narrow band filter having a frequency bandwidth adapted to a specific frequency. The system or processing unit may comprise a plurality of filters that simultaneously the received signal so as to simultaneously sense the medium at a plurality of other focal points $FP_j$. The filter(s) are preferably digital filters implemented by software in the processing unit 13.

All variants of the embodiment of FIGS. 2 and 2A are using only one signal $S_1$, the system only needs in this example one analog to digital converter to convert the signal $S_1$ into data. The quantity of the data that must be transferred to the processing unit 13 is consequently advantageously very small compared to prior art beamforming systems, and the cost of the system is greatly reduced.

Figure 3:
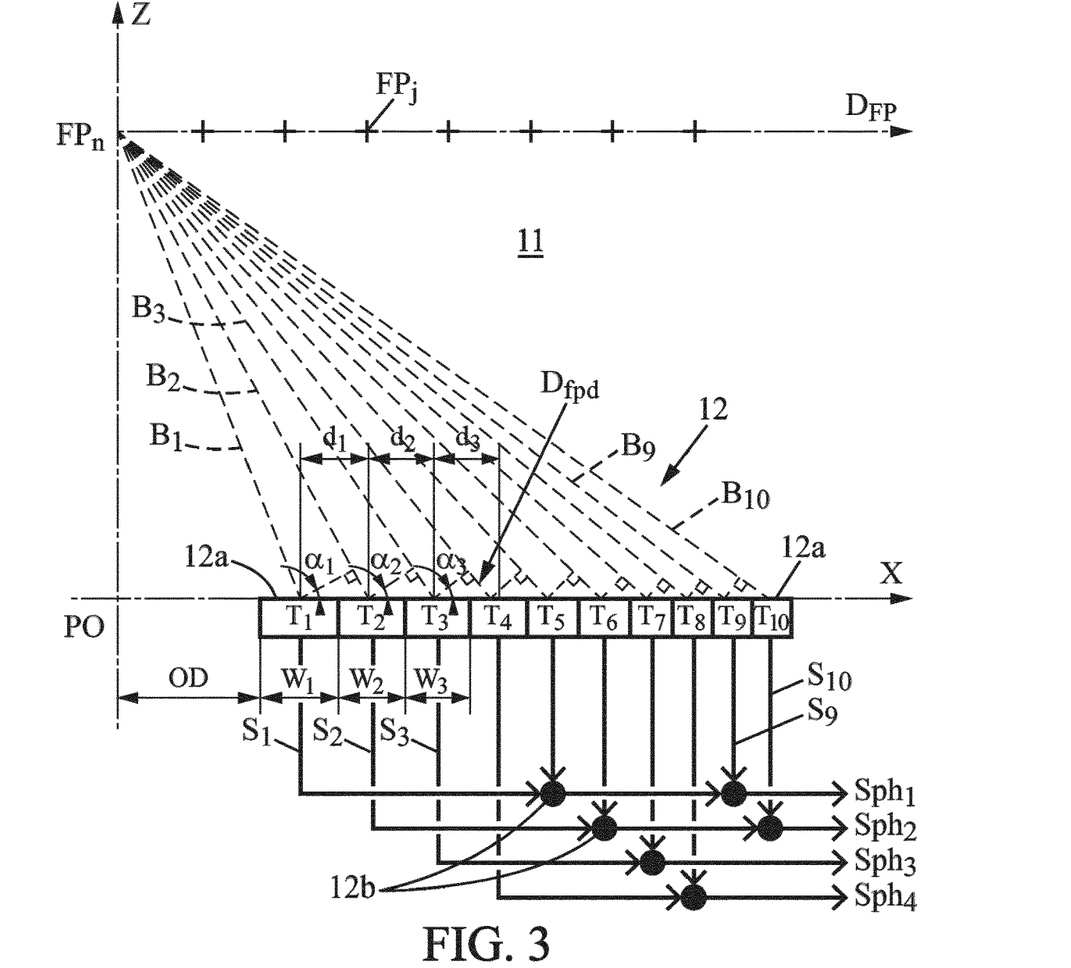
FIG. 3 is a schematic view of a second embodiment of a system according to the invention.
Figure 3A:
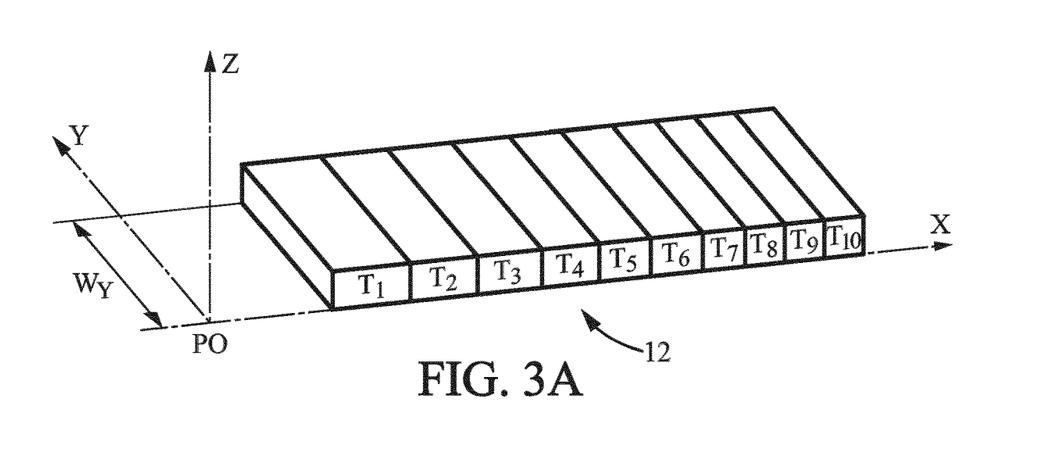
FIG. 3A is a perspective view of the probe of FIG. 3.

FIG. 3 shows a view in the X-Z plane of the probe and processing according to another embodiment of the disclosure. FIG. 3A shows the probe of FIG. 3 in a perspective view illustrating that the probe of the current disclosure is not an axisymmetric probe and that this probe is a linear probe aligned in the longitudinal direction X.

In this embodiment, the probe 12 comprises a plurality of transducer 12a, aligned according to the longitudinal direction X. Each transducer 12a is also referred as $T_i$, i being an index of the transducer, i being a positive non-null integer, and comprised between 1 and N (inclusive). Each transducer $T_i$ receives and/or generates a signal $S_1$, identified by same index i of the corresponding transducer $T_i$.

The transducers $T_i$ correspond to the probe sections having a width that decrease from a first end (left side of probe 12 on FIG. 2) to a second end (right side of probe 12 on FIG. 2) of the probe: i.e. the widths $w_1$, $w_2$, $w_3$, . . . .

The nominal focal point $FP_n$ is situated inside the medium 11 and in a depth direction Z perpendicular to the longitudinal direction X. The longitudinal direction X and depth direction Z intersects at a point of origin PO. A first transducer $T_1$ situated at a left lateral edge of the probe, is offset from this point of origin PO: They are distant of an offset distance OD. Each transducer $T_i$ emits and/or receives a portion an ultrasound wave, i.e an ultrasound beam Bi directed to the nominal focal point $FP_n$.

The transducers 12a are configured so as any pair of two transducers $(T_i, T_{i+1})$ that are neighbour one to the other have a focal point difference distance $D_{fpd}$ equal to the wavelength λ divided by a period number p. The focal point difference distance $D_{fpd}$ is therefore a constant value for the probe 12.

The period number p is an integer greater or equal to two (2). In the figure, the period number p is equal to four (4), and the focal point difference distance $D_{fpd}$ is equal to λ/4.

The focal point difference distance $D_{fpd}$ is an absolute value of a difference between a first distance between the nominal focal point $FP_n$ and the first transducer $T_i$ of index i belonging to the pair of two transducers $(T_i, T_{i+1})$ (length of first beam $B_i$) and a second distance between the nominal focal point $FP_n$ and the second transducer $T_{i+1}$ of index i+1 belonging to the pair of two transducers $(T_i, T_{i+1})$ (length of second beam $B_{i+1}$).

In other words, for each pair of neighbour transducer $(T_i, T_{i+1})$ in the probe 12, the focal point difference distance $D_{fpd}$ is as follow:

$$D_{fpd} = |d(FP_n, T_i) - d(FP_n, T_{i+1})| = \lambda/p \qquad (Eq.\ 2)$$

where
  $d(FP_n, T_i)$ is the first distance (length of first beam $B_i$),
  $d(FP_n, T_{i+1})$ is the second distance (length of second beam $B_{i+1}$),
  i is an index of any transducer, and
  λ is the wavelength of ultrasound waves in the medium 11.

In the embodiment of FIG. 3, a distance to any transducer $T_i$ is for example defined at the geometric center of said transducer, but any other definition can be used; e.g. a distance on the left edge of the transducer, or on the right edge of the transducer, or any other definition.

In this embodiment, as all transducers are aligned according to a longitudinal direction X that is a straight line, and because of the above relations, the transducers 12a are configured with a width $w_i$ that changes along said longitudinal direction X: e.g. the second transducer $T_2$ has a width $w_2$ that is shorter than the width $w_1$ of the first transducer $T_1$, and so on for all of them. The transducer's widths $w_i$ are consequently shorter and shorter when going away from the point of origin PO.

Additionally, the beams $B_i$ (line $FP_n$-$T_i$) from the nominal focal point $FP_n$ are more and more inclined when going away from the point of origin PO.

Figure 4:
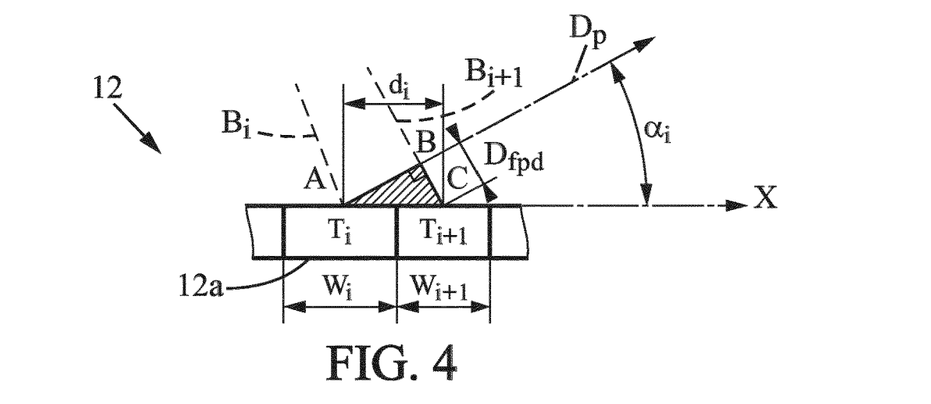
FIG. 4 is a detailed view of the probe of FIG. 3.

FIG. 4 is a generalized and enlarged view of two neighbour transducers $T_i$, $T_{i+1}$. A rectangle triangle (A, B, C) hatched on this FIG. 4 is defined for each pair of neighbour beams $(B_i, B_{i+1})$. The focus point difference distance $D_{fpd}$ is represented on this figure, and one can deduce the following relation:

$$D_{fpd} = d_i \sin(\alpha_i) = \lambda/p \qquad (Eq.\ 3)$$

where
  $d_i$ is the distance between the center of transducer $T_i$ to the center of next (neighbour) transducer $T_{i+1}$, so this distance is equal to:

$$d_i = (w_i + w_{i+1})/2, \text{ and}$$

$\alpha_i$ is the angle between the longitudinal direction X and a direction $D_P$ perpendicular to the next beam direction $B_{i+1}$.

Then, the wavelength λ corresponds to a full period of ultrasound wave having a phase varying between zero radian to 2·π radians. As the focus point difference distance $D_{fpd}$ is a constant value equal to λ/p, the signals $S_i$, $S_{i+p}$, $S_{i+2p}$ . . . respectively from transducers $T_i$, $T_{i+p}$, $T_{i+2p}$, . . . have the same phase, i.e. phase 0, phase (λ/p)·p=2·π, phase (λ/p)·2p=4·π . . . . Therefore, these signals are "in phase" and can be directly added by short circuits from lines at the "in-phase" transducers 12a, as represented in FIG. 3. The short circuits 12b are adding the electric charges of the "in phase" transducers 12a (e.g. piezo transducers) and are providing a phase signal $Sph_m$, m being an index of phase signal representing the group of "in-phase" transducers. However, other solutions may be used by a skilled man depending on transducers technology.

In other words, the signals $S_i$ from the transducers $T_i$ that are p-spaced one to another are added (e.g. by short circuits) to form a phase signal $Sph_m$. The short circuits of this embodiment are performing a kind of analog addition of the signals from transducers.

In other words, the phased signals $Sph_m$ are defined as follow:

$$Sph_m = \sum_k S_{m+k \cdot p} \quad \text{(Eq. 4)}$$

where
- $S_i$ is a signal from a transducer ($T_i$) of index i,
- m is a phase signal index, with m∈[1, p],
- k is takes possible values for the index of transducers, and
- p is the period number.

Then, the system comprises N signals $S_i$ of transducers (i.e. the number of transducers in the probe). But the system comprises only p phased signals $Sph_m$.

As period number p is an integer that can be relatively small (two or four for instance), the number of phased signals $Sph_m$ is relatively small.

This advantageously reduces the number of analog to digital converters needed to convert the phased signals into data in comparison to the number of transducers. This reduces the quantity of said data that must be transferred to the processing unit 13, and as a consequence it reduces the cost of the system.

Thanks to the above features, the probe 12 behaves as a Fresnel lens that focusses the ultrasound waves towards and from the nominal focal point $FP_n$ inside the medium 11.

As illustrated on FIG. 3A, the probe 12 is a linear probe extending along longitudinal direction X, said probe having a plurality of transducers 12a forming the probe sections. Such probe 12 is not axisymmetric, and is not symmetric. Therefore, contrary to axisymmetric probes, such probe 12 is able to focus to various focal points $FP_j$ that can be shifted laterally in the longitudinal direction X (direction of such linear probe).

The probe 12 has for example a constant width in the transversal direction Y, as illustrated on FIG. 3A. However, in another embodiment, such transversal width $w_Y$ can vary along the abscissa in the longitudinal direction X. For example, the transversal width can increase from the first end (left side of probe 12 on FIG. 3) to the second end (right side of probe 12 on FIG. 3) of the probe 12.

The processing unit 13 receives the p phased signals $Sph_m$, and only needs to "rephrase" these signals via a combining process on this reduced number (p) of phased signals so as to form a combined signal $S_1^*$ that then allows to sense the medium 11. Then, the processing unit 13 may determine values of pixels of an image representing said medium. This combination is for example a beamforming process as it is well known, but based on the p phased signals, and not all the signals $S_i$ from the transducers 12a.

Thanks to the above features (the probe 12 comprising a plurality of transducers 12a and the addition of the p-spaced signals Si and the combination of phased signals $Sph_m$), the ultrasound system 10 behaves as a Fresnel lens that focusses the ultrasound waves towards and from the nominal focal point $FP_n$ inside the medium 11.

Then, the processing unit 13 is able to implement the first or second variant of the first embodiment, i.e. the processing unit is able to emit a plurality of successive frequencies $f_j$ to move the focal point or the processing unit 13 is able to emit a wave having a broadband characteristic and to filter the receive signal, as explained in the first embodiment. The focal point is moved successively or virtually simultaneously inside the medium 11 towards other focal points $FP_j$ corresponding to said frequencies $f_j$. The other focal points are aligned on a direction of focal points $D_{FP}$ (the locus of a plurality of focal points by varying the frequency). The direction of focal points $D_{FP}$ might be substantially parallel to the longitudinal direction X, or inclined relative to the longitudinal direction X, or is a predetermined set of positions relative to the probe 12.

Then, the processing unit 13 can calculate an image of a region of interest inside the medium on the bases of the p phased signals $Sph_m$ received from the probe at the plurality of frequencies $f_j$. The image is for example composed of a grid of pixels in X-Z directions. It is understood that the abscissa x of a pixel in the longitudinal direction X is determined by varying the frequency f and the ordination z of a pixel in the depth direction Z is determined by the level of a processed signal received for each time of flight (distance to transducer) as it is well known in ultrasound imaging.

In this embodiment, the virtual "Fresnel lens" is digitally recomposed by the configuration of the transducers 12a (their geometry) and the additions of the p-spaced signals from the probe 12. This corresponds to a virtual Fresnel lens that uses discrete (discontinuous) physical elements (transducers) and a specific combination of signals, whereas, in the first embodiment, the simulated Fresnel lens is a continuous physical element (a transducer and a lens layer).

Figure 5:
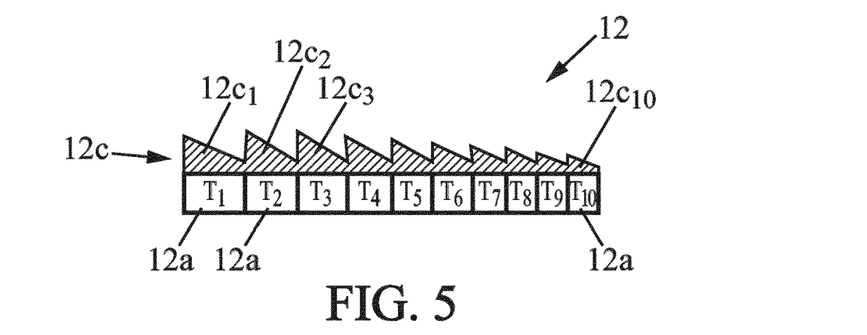
FIG. 5 is an optional modification of the probe of FIG. 3, including a patterned lens layer.

According to another variant of this second embodiment represented on FIG. 5, the probe 12 further comprises a patterned lens layer 12c positioned above the transducers 12a and in contact with the transducers 12a and in contact with the medium 11. The patterned lens layer 12c is adapted for optimizing the emitted and received ultrasound waves between each transducer $T_i$ and the nominal focal point $FP_n$. This patterned lens layer 12c provides a correction so as the upper surface of each transducer $T_i$ receives an "in-phase" ultrasound wave by correcting time of flight differences between a left end and a right end of each transducer.

To this purpose, the patterned lens layer 12c may have a shape which looks like a saw tooth shape like the lens layer of first embodiment. This shape comprises a plurality of sections, each section facing one transducer $T_i$ in the plurality of transducers.

For example, the patterned lens layer 12c comprises sections $12c_1$, $12c_2$, $12c_3$, . . . , respectively corresponding to the transducers $T_1$, $T_2$, $T_3$, . . . .

Each section of the patterned lens layer has a thickness that increases on the side of the transducer $T_i$ that corresponds to the shortest distance to the nominal focal point $FP_n$ (left end of each transducer in case of the FIG. 5).

Figure 6:
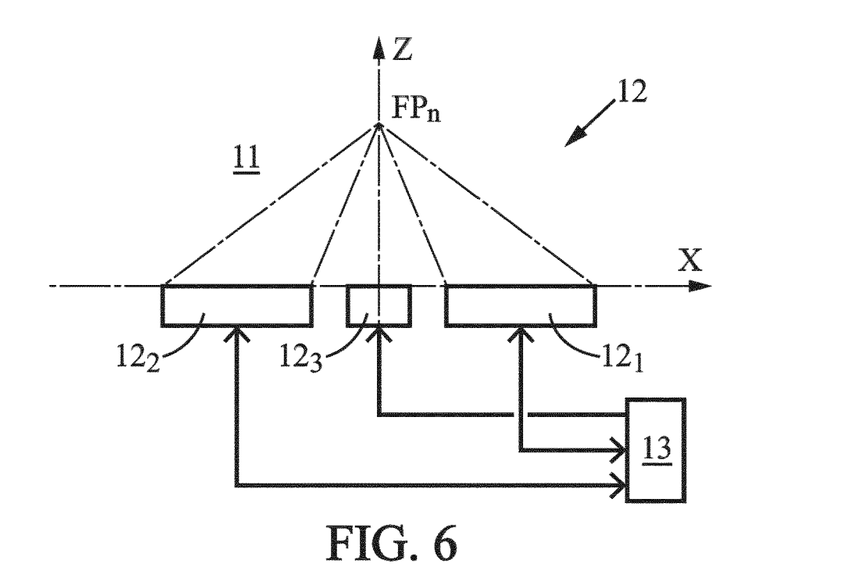
FIG. 6 is a schematic view of a third embodiment of a system according to the invention, including a probe having two portions as disclosed in FIG. 2 or FIG. 3, and having an additional transducer between thereof.

FIG. 6 shows a view of the probe and processing according to another embodiment of the disclosure. This figure is a view in XZ plane. But, similarly to the previous embodiments, the probe 12 is not an axisymmetric probe and it is a linear probe that extends according to the longitudinal direction X. The probe 12 may have a constant width $W_Y$ in the transversal direction Y or a width $W_Y$ in the transversal direction Y depending on the abscissa in the longitudinal direction as already explained.

In this third embodiment, the probe 12 comprises at least two portions of probes, a first portion $12_1$ and a second portion $12_2$.

The first portion $12_1$ is for example situated at a first side in comparison to the depth direction Z (in plane X-Z), i.e. on right side on FIG. 6, and the second portion $12_2$ is situated at a second side in comparison to said depth direction Z, said second side being opposite to the first side in comparison to the depth direction Z. In other words, the depth direction Z is located between the first portion $12_1$ and the second portion $12_2$.

Therefore, the two portions of probe $12_1$, $12_2$, are situated on both sides of the depth direction Z, and are each one oriented in the same direction Z, facing the medium 11 so as to be able to generate and to receive ultrasound waves from this medium 11 (in the upper half plane X-Z on FIG. 6).

The fist portion $12_1$ focusses ultrasound waves towards a first nominal focal point $FP_{n1}$, and the second portion $12_2$ focusses ultrasound waves towards a second nominal focal point $FP_{n2}$. The two nominal focal points $FP_{n1}$, $FP_{n2}$ may be separate one from the other so as to elongate (in the longitudinal direction X) the optimum well focussed area inside the medium 11. Reciprocally, the two nominal focal points $FP_{n1}$, $FP_{n2}$ may be the same point (i.e. superposed) so as to improve the accuracy of the image.

The first portion $12_1$ focusses in a first inclined direction (e.g. upper left) whereas the second portion $12_2$ focusses in a second inclined direction (e.g. upper right), the second direction being different to the first direction, and for example opposite relative to the longitudinal direction X Then, the first and second portions $12_1$, $12_2$ of the probe 12 may be realized according to the technical features above described in the first embodiment or in the second embodiment, i.e. with a single transducer or a plurality of transducers. The two portions may advantageously be of same type.

The processing unit 13 of the third embodiment is then adapted to determine:
- a first image I1 on the bases of signals and/or phased signals from the transducers belonging to the first portion $12_1$ of the of the probe 12, and
- a second image I2 on the bases of signals and/or phased signals from the transducers belonging to the second portion $12_2$ of the probe.

The first image I1 may correspond to an image that is build or calculated for pixels corresponding to focal points located on the first side (right), i.e. in the first quadrant XZ defined in the first side relative to the depth direction. The first quadrant XZ is the quadrant in the XZ plane that extends in the positive longitudinal direction X and in the positive depth direction Z.

The second image I2 may reciprocally correspond an image that is build or calculated for pixels corresponding to focal points located on the second side (left), i.e. in the second quadrant −XZ defined in the second side relative to the depth direction. The second quadrant −XZ is the quadrant in the XZ plane that extends in the negative longitudinal direction X and in the positive depth direction Z.

The processing unit 13 then can move the focal point from left to right in the first quadrant XZ of the first portion $12_1$ (i.e. in the positive direction of longitudinal direction X) by increasing the frequency f analysed in the signals from the first portion $12_1$, and it may move the focal point from right to left in the second quadrant −XZ of the second portion $12_2$ (i.e. in the negative direction of longitudinal direction X) by increasing the frequency analysed in the signals from the second portion $12_2$. Therefore, the two portions $12_1$, $12_2$ of probe 12 are working symmetrically each one in his plane quadrant for providing signals used to build or calculate pixel in each associated respective quadrant of the plane XZ, i.e, the first or the second quadrant. In this case, the two portions $12_1$, $12_2$ can be symmetric relative to the depth direction Z, and they provide first image I1 and second image I2 that are scanned symmetrically relative to the depth direction Z if considering increasing frequency for both portions of probe 12.

Then, the processing unit 13 determines the pixels of the image representing a region of interest ROI of the medium 11 on the bases of the first and the second images I1, I2.

Eventually, the processing unit 13 directly determines the pixels of the image representing the region of interest ROI of the medium 11 on the bases of the signals and/or phased signals from the first and second portions $12_1$, $12_2$ of the probe 12, i.e. without calculating intermediate first and second images.

The region of interest of such embodiment having a first and second portion of probe 12 may be wider in X direction.

In a variant represented on FIG. 6, the system comprises an additional transducer $12_3$. This additional transducer $12_3$ may be positioned between the first and second portions $12_1$, $12_2$ of the probe 12. This additional transducer $12_3$ may be adapted so as to focus ultrasound waves on the line of the depth direction Z, between the first and second portions $12_1$, $12_2$ of the probe.

The additional transducer $12_3$ may be adapted so as to generate an ultrasound wave of a frequency lower than the first and second portions $12_1$, $12_2$ of the probe 12.

Optionally, the additional transducer $12_3$ is adapted to generate a low frequency vibration inside the medium, whereas the first and second portions $12_1$, $12_2$ of the probe are adapted to higher frequencies that are used for determining an image or a plurality of time successive images of the same region of interest ROI inside the medium 11.

Then, the first and second portions 121, 122 of the probe are used by the processing unit 13 so as to sense and/or image the propagation of the vibration inside the medium 11. The time successive images are then combined by the processing unit 13 so as to calculate at least one value of elasticity of at least one point inside the medium 11, on the bases displacements of said vibration.

Ideally, the system 10 is also able to calculate or determine an image of elasticity of the region of interest ROI in the medium.

Such particular embodiment provides an elasticity imaging device that is particularly of low cost. Such small and economic system is usable in numerous new medical imaging applications.

The above embodiments are provided for illustration purposes only and may be combined in totality or in part, the protection provided by this application being defined by its set of claims.

Thanks to the various technical features of above embodiments, the ultrasound system needs less electronic components than prior art systems. The system is then less costly.

The system 10 according to the disclosure also spends less energy in use. It can be easy to carry, and small enough to be a portable system.

Moreover, it is also easier to manufacture. Therefore, the ultrasound system is much less costly.

Such system 10 can be less heavy, and therefore more easy to use for the user.

The invention claimed is:

1. An ultrasound system comprising:
a probe adapted for being put into contact with a medium and comprising at least one transducer adapted for emitting and receiving ultrasound waves in said medium, and
a processing unit associated to said probe and adapted for processing signals from the probe,
said ultrasound system being characterized in that:
the probe is not axisymmetric and is a linear probe extending according to a longitudinal direction,
the probe comprises at least one portion comprising along the longitudinal direction a plurality of probe sections having a width that decrease from a first end to a second end of said portion so as to behave as a Fresnel lens in that the probe focusses the ultrasound waves towards and from a focal point inside the medium, said focal point being different for each frequency of said ultrasound waves, and
the processing unit analyses signals received from said probe at a plurality of frequencies around a nominal frequency for sensing the medium at a plurality of focal points situated in the medium, and
the processing unit builds an image of the medium on the bases of a plurality of focal points sensed in the medium, the image being composed of a grid of pixels, the pixels aligned in the longitudinal direction being determined by the signals at the plurality of frequencies, and the pixels aligned in the depth direction perpendicular to the longitudinal direction being determined by the level of the signals received for a plurality of time of flight between the probe and focal point in the medium.

2. The system according to claim 1, wherein the processing unit controls the probe to emit successively at the plurality of frequencies to move the focal point in the medium, and the processing unit analyses the signals received for each of said frequencies for sensing the medium at said focal points.

3. The system according to claim 1, wherein the processing unit controls the probe to emit a ultrasound wave having a broadband characteristic around the nominal frequency, and filters the signals at a plurality of frequencies for sensing the medium at said plurality of focal points.

4. The system according to claim 1, wherein:
the probe comprises one transducer and a lens layer disposed above said transducer, the lens layer being composed of a plurality of sections forming a quasi-saw tooth shape, each section having a step length in the direction of the nominal focal point that is equal to a distance defined so that an ultrasound wave emitted by the transducer in the medium through the lens layer has a phase difference of $2 \cdot k \cdot \pi$ between a portion of wave emitted though one section and a portion of wave emitted by a neighbour section, next to said one section, k being an integer greater or equal to one.

5. The system according to claim 4, wherein the step length is equal to:

$$SL = \lambda_{lens} \cdot c_{medium} / (c_{medium} - c_{lens})$$

where
$c_{medium}$ is a speed of ultrasound wave inside the medium,
$\lambda_{lens} = c_{lens}/f_n$ is the lens wavelength $\lambda_{lens}$,
$c_{lens}$ is a speed of ultrasound wave inside the material of the lens layer, and
$f_n$ is the nominal frequency of the ultrasound wave adapted for focusing to the nominal focal point.

6. The system according to claim 1, wherein:
the probe comprises a plurality of transducers that are configured so as any pair of two transducers that are neighbour one to the other have a focal point difference distance equal to the wavelength divided by a period number p, said period number p being an integer greater or equal to two, the focal point difference distance being an absolute value of a difference between a first distance between the nominal focal point and the first transducer belonging to the pair and a second distance between the nominal focal point and the second transducer belonging to the pair, and
the system adds signals from transducers that are p-spaced one to another to form p phased signals.

7. The system according to claim 6, wherein the focal point difference distance is determined as follow:

$$D_{fpd} = |d(FP, T_i) - d(FP, T_{i+1})| = \lambda/p$$

where
d is the first distance,
d is the second distance,
i is an index of any transducer,
$\lambda$ is the wavelength, and
p is the period number.

8. The system according to claim 6, wherein the p-spaced transducers are connected together with short circuits to add the signals from said p-spaced transducers to form the phased signals.

9. The system according to claim 6, wherein the period number is equal to four.

10. The system according to claim 6, wherein the probe further comprises a patterned lens layer positioned above the transducers and arranged to be put in contact with the transducers and with the medium.

11. The system according to claim 10, wherein the patterned lens layer is a prismatic shape, having a thickness that increases on the side of the transducer that corresponds to the shortest distance to the nominal focal point.

12. The system according to claim 1, wherein the probe comprises two portions, a first portion situated on a first side in comparison to a depth direction, said depth direction being perpendicular to the longitudinal direction, and a second portion situated on a second side of said depth direction.

13. The system according to the claim 12, wherein the first portion and second portion are symmetric relative to the depth direction, the first portion and second portion each have a nominal focal point, and said nominal focal points are identical.

14. The system according to claim 12, wherein the processing unit builds a first image with signals from the first portion and a second image with signals from the second portion, said first and second images not overlapping each other, the first image corresponding to a first quadrant in the medium defined in the first side relative to the depth direction, and the second image corresponding to a second quadrant in the medium defined in the second side relative to the depth direction.

15. The system according to claim 13, wherein the probe further comprises at least one additional transducer situated between the first and second portions.

16. The system according to claim 15, wherein the additional transducer is adapted for generating a vibration propagating inside the medium at a low frequency, said vibration being sensed by the first portion and second portion of the probe, and the processing unit calculates at least one value of elasticity inside the medium on the bases of displacement of said vibration in the medium.

* * * * *